United States Patent [19]

Beran

[11] 4,114,626
[45] Sep. 19, 1978

[54] INTUBATION SET

[76] Inventor: Anthony V. Beran, 3802 Teakwood St., Santa Ana, Calif. 92707

[21] Appl. No.: 759,181

[22] Filed: Jan. 31, 1977

Related U.S. Application Data

[63] Continuation of Ser. No. 545,434, Jan. 30, 1975, abandoned.

[51] Int. Cl.² ............................................. A61M 25/02
[52] U.S. Cl. .................................... 128/348; 128/133; 128/DIG. 26; 248/205 A; 285/177
[58] Field of Search ................... 128/348–351, 128/133, 214 R, 214.4, 347, DIG. 26, 276–278; 215/307; 248/205 A; 285/177; 24/5,-73 HS

[56] References Cited

U.S. PATENT DOCUMENTS

| 443,680 | 12/1890 | Johnson | 285/177 |
|---|---|---|---|
| 2,820,457 | 1/1958 | Phillips | 128/351 |
| 2,821,194 | 1/1958 | Simmons | 128/214 R |
| 2,898,917 | 8/1959 | Wallace | 128/350 R |
| 2,941,532 | 6/1960 | Borin | 128/276 |
| 3,046,989 | 7/1962 | Hill | 128/348 |
| 3,138,158 | 6/1964 | Gordon et al. | 128/133 |
| 3,177,284 | 4/1965 | Stuessel | 285/177 X |
| 3,241,554 | 3/1966 | Coanda | 128/350 R |
| 3,334,628 | 8/1967 | Saemann et al. | 128/276 |
| 3,357,429 | 12/1967 | Folkman et al. | 128/275 |
| 3,545,443 | 12/1970 | Ansari | 128/347 |
| 3,677,250 | 7/1972 | Thomas | 128/348 |
| 3,745,999 | 7/1973 | Deaton | 128/277 |
| 3,783,876 | 1/1974 | Dye | 128/347 |
| 3,854,483 | 12/1974 | Powers | 128/349 R |

Primary Examiner—Dalton L. Truluck
Attorney, Agent, or Firm—Grover A. Frater

[57] ABSTRACT

An intubation set is disclosed which incorporates a special fastening means by which the tube can be fixed conveniently and effectively to the body of a patient at a point adjacent to the body opening into which the tube has been inserted. The set includes a special connector by which it may be securely associated.

12 Claims, 22 Drawing Figures

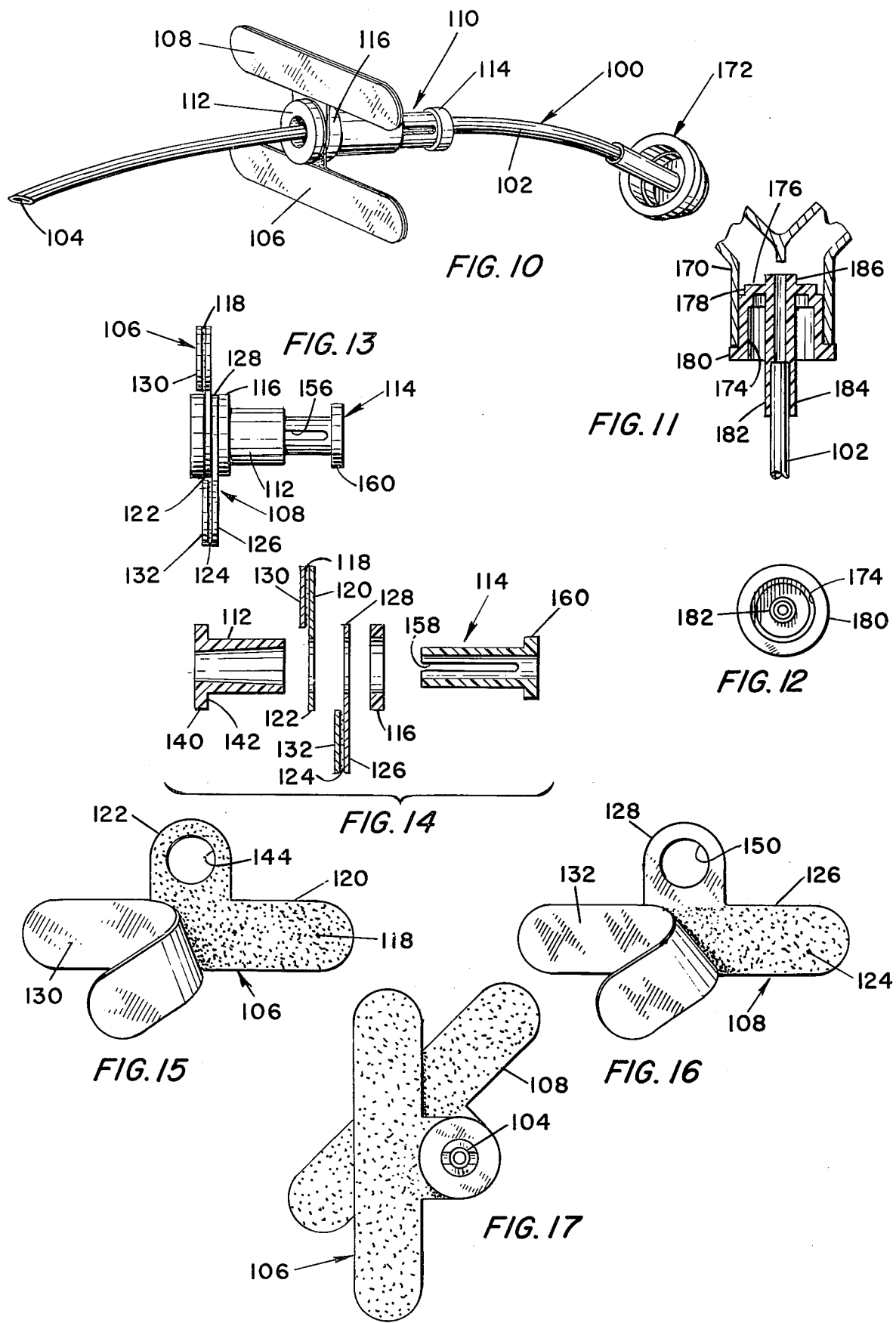

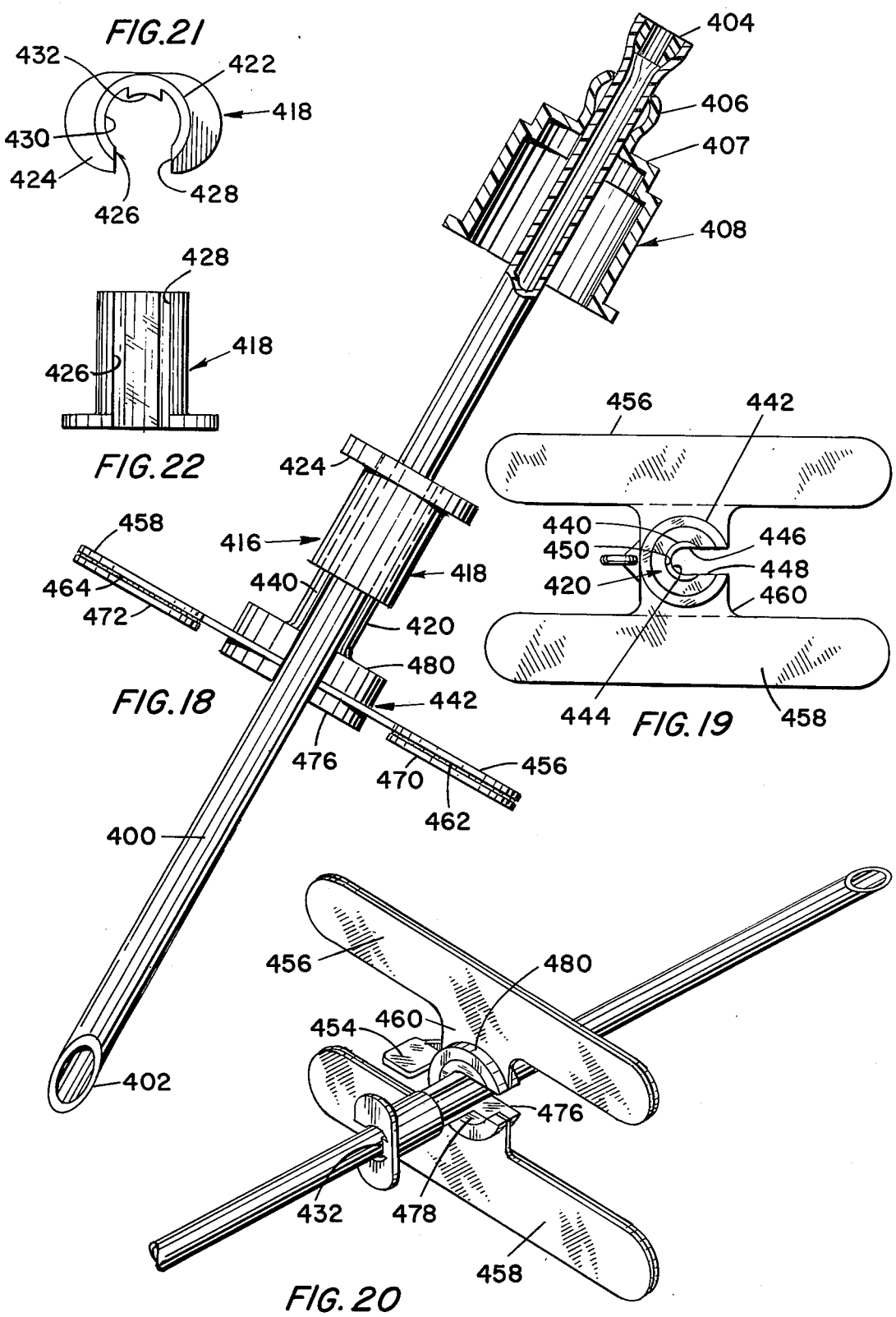

INTUBATION SET

This application is a continuation of application Ser. No. 545,434, filed Jan. 30, 1975 by Anthony V. Beran for INTUBATION SET, now abandoned, which was application Ser. No. 439,374, filed Feb. 4, 1974 by Anthony V. Beran for INTUBATION SET, abandoned, which was application Ser. No. 360,250, filed May 14, 1973 for INTUBATION SET by Anthony V. Beran, also abandoned.

This invention relates to improved structures for holding apparatus in position in front of a subject's mouth or other body opening. In particular, it relates to an improved intubation set and to an improved fastening and connecting structure for holding such a set in place.

A number of procedures, particularly medical procedures, involve insertion of tubes into a patient's or a subject's body openings. The invention provides an improved holding structure by which that tube can be held in a selected position notwithstanding movement of the patient or subject. While the fastening element and connecting element of the invention are useful in connection with most tubes, they are particularly useful in the intubation set of the invention. Thus, the object of the invention is not only to provide an improved holder and an improved connector element, but it is also an object to provide an improved intubation set employing the holder and connector.

It is an object to provide an intubation set and connector and holder, and an intubation set which is convenient to use, and which can be applied without modification other than cutting the tube to length, to a wide variety of medical and other procedures; and which are so inexpensively produced that they can ordinarily be disposed of after having been used once.

It will be apparent from the description of the invention that it is applicable to a wide variety of circumstances in which it is required to hold a tube in some selected position for any purpose. However, the invention is particularly applicable to those situations where it is desired to insert a tube in a body opening and then to fix the tube so that the degree of insertion cannot change while permitting a maximum degree of movement of or by the patient.

The practice in the past has been to insert a tube into the patient's body opening, and then, using adhesive tapes, to secure the standing part of the tube to the patient's body by applying tape over or around the tube and to the patient's skin. As often as not, the direction of the tube at the point of entry was determined not by consideration of patient comfort or the function to be performed by the tube, but rather by the mechanical problem of getting the tube fixed in place. This invention solves that difficulty by making it possible to position the tube in the manner calculated by the attendant to be least uncomfortable and most effective functionally, and then to secure the tube to the patient in that position, whatever that position might be. The satisfactory fastening in place of a nasal-tracheal tube is particularly difficult because of the substantial amount of discomfort involved in having a tube extending through one's nasal passages or mouth. The other end of the tube is usually connected to some treatment or test apparatus, the position of which is fixed. Movement of the subject causes movement of the tube relative to the treatment or test apparatus. The invention provides an improved connection element for the connection of the tube and that apparatus.

The accompanying drawings show two embodiments of the invention. They show what are considered to be the best of several embodiments that are now envisioned.

In the drawings:

FIG. 10 is a pictorial view of another embodiment of the invention;

FIG. 11 is a view partly in section and partly in elevation illustrating how the apparatus of FIG. 10 is connected to the output element of a respiratory apparatus;

FIG. 12 is a view in end elevation of the connecting element shown in FIGS. 10 and 11;

FIG. 13 is a view in elevation of the attaching element and adhesive patches;

FIG. 14 is an exploded view of the parts that make up the fastening member and adhesive patch assembly of FIG. 13 shown in a section taken on a plane that contains the axis of the fastening member;

FIGS. 15 and 16 are views in elevation of the patches of FIG. 1 shown with their protective covers peeled partly away;

FIG. 17 is a view in end elevation of the set of FIG. 10 shown with one patch rotated and protective covers removed;

FIG. 18 is a view partly in elevation and partly in section of another embodiment of the invention;

FIG. 19 is a top view of the patches and part of the holder of FIG. 18;

FIG. 20 is an isometric view of part of the set of FIG. 18; and

FIGS. 21 and 22 are a top and front elevational view, respectively, of part of the holder of FIG. 18.

Figure 1:
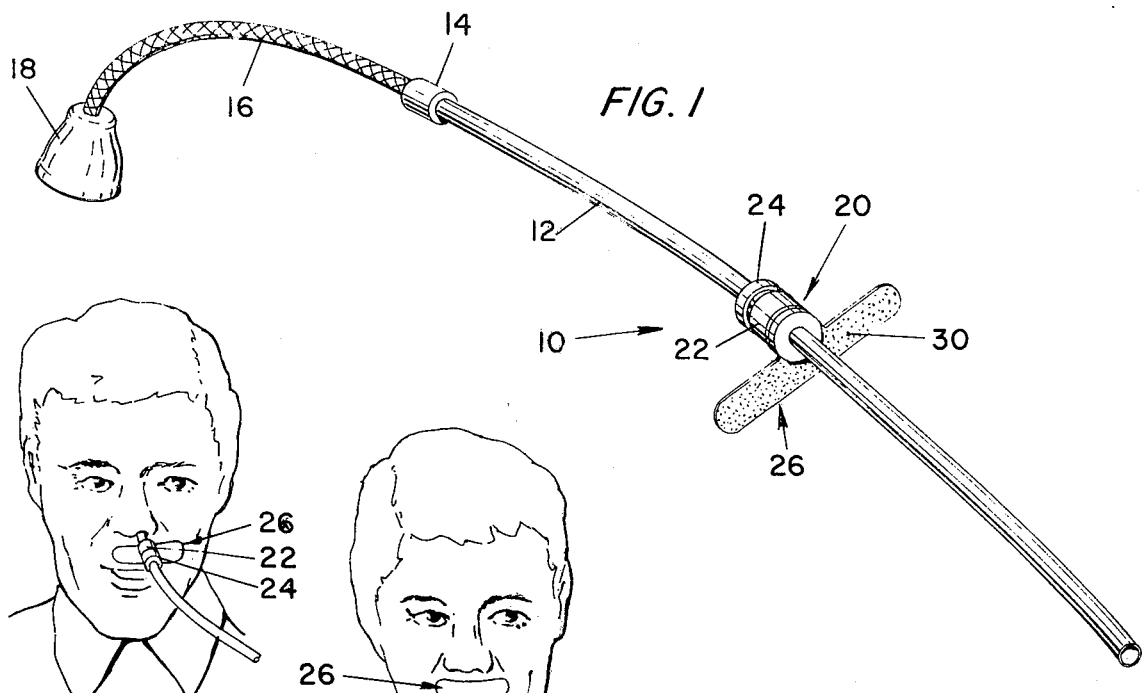
FIG. 1 is a pictorial view of an intubation set embodying the invention.

The several elements in FIG. 1 are shown assembled into an intubation set which is generally designated by the numeral 10. The set includes a tube 12 which in preferred form is made of a non-toxic, flexible, and somewhat resilient plastic material. It is shaped to form a tube having, in this case, an outer diameter of about one-fourth of an inch. The upper end of that tube 12 is insertable into a collar 14 whose other end is fixed to a flexible tube 16. The wall of the tube is molded upon a helical wire to form a section of conduit that can be bent on a small radium without collapsing. The other end of the tube is fixed to a coupling or fitting 18 which can be connected to respiratory support apparatus. When the tube 12 is inserted in the body opening of a patient or subject, communication is afforded from the fitting 18 through the conduit 16 and coupling 14 and tube 12 to the interior of the patient. Ordinarily, the tubing is inserted in whatever degree is appropriate. The upper end of the tubing is then removed from the coupling 14 and an appropriate part of the tube is cut away to reduce its length as desirable and then the end of the tubing is reinserted into the coupling 14.

Fitting 18 is often connected to an apparatus whose position is fixed. In that circumstance, movement of the patient might alter the degree of insertion of the tube. Whether to prevent that or accomplish some other purpose, it is ordinarily desirable or required to fix the tubing at some point along its length to the patient so that the degree of insertion cannot be altered as the patient is moved. This intubation set includes a fastening means generally designated 20 which will accomplish that purpose. That fastening means comprises three main parts in this embodiment. One of those parts is a body through which the tube extends. In this case, the body 22 is a sleeve which is provided with an axial bore through which the tube extends. Another of those parts is a clamping element 24. It cooperates with the tube and the sleeve 22 to clamp the tube against axial movement. The clamping element is arranged so that the tube can be released whereby it can be moved axially and can be entirely removed and subsequently replaced. If, as in the case shown, the clamping structure is a separate element from the body, then it is desirable that it be located toward the standing part of the tube 12 which is that part between the fastening means and the coupling 14.

The fastening means also includes, as its third part, a patch of flexible material which is fastened at one of its edges to the body part of the fastening means. The patch may be pliant or resilient or both. It is necessary that the patch be bent or reshaped when used so that it will lie over and contact a substantial surface area of the patient's skin. It is capable of lying in a plane that is substantially perpendicular to the direction in which the tube passes through the fastening means. A layer of adhesive material is applied to the side of the patch away from the standing part of the tube so that the adhesive material faces toward the patient's skin when the tube has been inserted.

In this preferred embodiment, the patch 26 extends laterally from the sleeve 22 at a point near the end of the sleeve toward the patient. It has the form of a strip which is fixed to the sleeve at one edge in the mid-region of its length. The adhesive layer in the preferred embodiment covers the whole of one side of that strip. If the adhesive does not cover the whole area, it should at least cover the region of the strip adjacent to the sleeve 22 and the regions at the ends of the strip.

Figure 4:
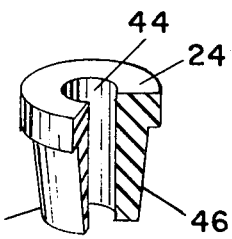
FIG. 4 is a view on cross-section of an improved fastening structure employed in the intubation set of FIG. 1 shown assembled on a section of tubing.

In one embodiment, the sleeve and the patch, or strip, are intregally formed of a plastic material. Because of its relative thinness, the strip is easily flexible. It is produced so that the strip extends laterally in the plane perpendicular to the axis of the bore. The plastic section is made somewhat thinner along a line at the junction between the sleeve and the strip to facilitate tilting the strip up from that plane by as much as 90 degrees. In the embodiment shown, the sleeve 22 comprises two sections made of plastic. One is a thin clamping member 19 that is formed with three projections that fit into recesses formed in the upper, longer section 23. The patch 26 in this case is cut from a sheet of medical adhesive tape. An attaching section is integrally formed with the patch or strip at the mid-region of one edge along the line 28. In this case, the attaching section 25 is toroidal and formed with three openings to receive the three projections of clamping member 19. The toroidal section is sandwiched between the clamping member 19 and sleeve section 23, as shown in FIG. 4, so that the axis of the openings in the toroidal section, the longer sleeve section, and the clamping member are all coincident.

Figures 2, 3, 9:
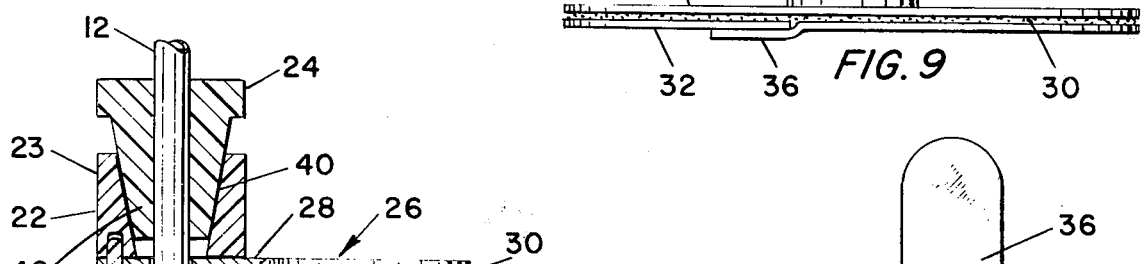
FIG. 2 is a pictorial view illustrating how the intubation set is fastened to a patient when the tube is inserted through the patient's nostril.
FIG. 3 illustrates how the intubation set can be applied to a patient when it is desired that the tube extend through his mouth.
FIG. 9 is a view in front elevation of the fastener assembly without its clamping member.
Figures 5, 6, 7:
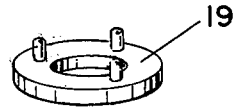
FIGS. 5, 6, 7 and 8 show the several individual parts that make up the fastening structure of FIG. 4.
Figure 8:
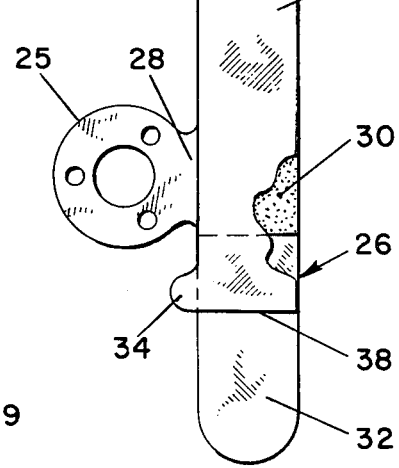

The lower face of the strip is covered with a coating of adhesive 30 and a protective sheet of plastic overlies that pressure sensitive adhesive. The protective sheet is best shown in FIGS. 4, 5 and 9. It consists of two overlapping pieces. One piece 32 extends over less than half of the strip and has a tab 34 extending to one side of the strip so that it can be grasped easily and peeled away from the adhesive. The other section of the protective covering is numbered 36. It extends over more than half of the length of the strip so that it overlaps the section 32. Its end 38 is easily lifted away from the section 32 so that it and section 36 can easily be peeled from the adhesive strip. The relation of these parts can be understood by comparison of the bottom view in FIG. 8 with the front elevational view of FIG. 9.

Returning to FIG. 4, the bore 40 in the sleeve 22 is tapered so that it has smaller diameter at the lower end or patient end of the bore. That bore accommodates the lower end 42 of the clamping element 24. The clamping element is itself provided with a bore 44 whose diameter is only slightly greater than the outside diameter of the tube 12 when the clamping member is in relaxed condition. It is made of a resilient material and has a narrow longitudinal section cut away at 46. The outer wall of lower end 42 is tapered. When the lower end 42 of the clamp is forced into the tapered opening 40, the lower walls of the clamp member are forced inwardly so that they will embrace and grip the outer surface of the tubing effectively clamping it against axial movement relative to the clamp and sleeve.

Other fastening arrangement involving wedge and screw principles are possible without departing from the invention. However, the embodiment shown in the preferred one. It is effective and inexpensive to manufacture and it can be clamped and unclamped with one hand.

FIGS. 2 and 3 illustrate two of the ways in which the intubation set may be used. In FIG. 2, the tube extends into the patient's nostril and it is held there by the fastening means. The protective covering for the adhesive strip has been removed and the pressure sensitive adhesive strip has been applied to the patient's upper lip. In the case shown, the fastening means is oriented so that the side of the strip to which the sleeve 20 is connected is toward the patient's nostril. The strip has been bent at its connection with the sleeve so that the axis of the bore through the sleeve is substantially parallel to the plane of the strip. In FIG. 3, the tube is inserted into the patient's mouth and the fastening member has its pressure sensitive adhesive strip pressed to the patient's upper lip. In this case, the sleeve is oriented with its bore substantially perpendicular to the plane of the adhesive strip.

It will be apparent that this arrangement of adhesive strip and body or sleeve in which one end of the sleeve is fixed to a mid-region at one edge of the sleeve makes the apparatus useful in a variety of different circumstances. Indeed, the flexible connection at one edge provides a kind of universal joint that makes the fastener easy to apply in a wide variety of circumstances. If, with time, the adhesive layer becomes less than entirely operative, the fastening member is easily removed from the tube and replaced after the tube is withdrawn from coupling 14.

The tube 12 in FIG. 1 is shown to be curved or arcuate along its length. That curve makes it easier to insert in certain body openings and particularly is advantageous in the case of nasal-tracheal tubes. The path that the tube follows is more or less curved and use of a curved tube facilitates its insertion. It will be apparent that the fastening member 20, and particularly the non-threaded clamping member 24, can be oriented rotationally relative to the tube in any degree. This is a fastener whose operation is not interrupted by use of a curved tube and conversely which has no tendency to reorient the tube when the clamping is effected. One of the advantages of the invention is that it can be used to interconnect a movable patient or subject with a fixed treatment or test apparatus, without becoming disconnected from the subject and without a change in the depth to which the tube end extends into the subject. The adhesive patch arrangement shown in FIGS. 1 through 9 is very effective in overcoming that difficulty. The embodiment shown in FIGS. 10 through 16 includes a second adhesive patch and that embodiment is even more effective in keeping the tube in position relative to the patient, both in terms of the strength of the connection to the patient and in terms of the variety of physical situations that can be accommodated. However, it is not enough that the intubation set be securely and conveniently attached to the patient or subject, it is also required that the other end of the tube be securely fastened to the respiratory set or other apparatus to which the patient is to be connected by means of the tube. The embodiment of FIGS. 1 through 9 shows one arrangement by which a secure connection can be made while permitting substantial degree of movement of the subject. The embodiment shown in FIGS. 10 through 17 shows another.

The connecting element shown in FIGS. 10, 11 and 12 can be produced so inexpensively that it can be treated as a throw-away item in circumstances in which the fitting 18, conduit 16 and coupler of 14 of FIG. 1 would not be thrown away because of their higher cost. Thus, the embodiment shown in FIG. 10 is one in which the complete intubation set, including the end connecting element, can be produced from inexpensive plastic. It can be considered as a throw-away structure. The set can be packaged in sterilized condition in an airtight plastic bag. The exterior of the bag can be gas-sterilized before use. Thus, this embodiment provides a convenient way to produce, transport, store, sterilize and use the set for the benefit of an individual patient and then to dispose of it without need to clean.

In FIG. 10, the intubation set is generally designated 100. It includes a tube 102 which has an end 104 for insertion into a body opening of a patient such, for example, as his nostril or his mouth. A pair of adhesive patches 106 and 108 are attached to the tube 102 at a selected point along its length by an attaching structure generally designated 110. That attaching structure is formed of three parts. One of them is an outer sleeve 112. The other is an inner, or clamping, sleeve 114, and the third part is a retaining ring 116.

The two patches 106 and 108 are shown in greater detail in FIGS. 15 and 16, respectively. The shape of these two patches is the same. They differ only in their adhesive layers. An adhesive layer 118 is formed on one surface of the patch sheet 120. It extends over and covers the surface of the tab 122 of patch 106. On the other hand, the adhesive layer 124 that overlies one surface of the patch sheet 126 of patch 108 does not extend over the tab 128 of that sheet. The one-piece, peel-away protective covering 130 of patch 106 is identical, in this embodiment, to the one-piece, peel-away protector 132 that covers the adhesive layer 124 of patch 108.

The manner in which the patches and the fastening element are assembled is illustrated in FIGS. 13 and 14. The clamping sleeve 114 and the retaining ring 116 are disassembled from the outer sleeve 112.

As best shown in FIG. 14, the sleeve 112 is formed with a flange 140 at one end whereby a shoulder surface 142 is provided. The shoulder surface faces toward the direction in which the sleeve extends from the flange. Patch 106 is assembled on the sleeve 112 such that the sleeve extends through the opening 144 of tab 122. The adhesive layer faces toward the surface 142 of the flange, and the area around the tab opening 144 is pressed against surface 142. A portion of the adhesive layer 118 around the opening is effective to bond the patch sheet 124 to the surface 142. The peel-away protector 130 is pressed against the elongated part of the patch so that it covers and protects the adhesive layer 118, except at the tab 122.

The patch 106 having been assembled with the sleeve 112, the patch 108 is next assembled on the sleeve by passing the sleeve through the opening 150 in tab 128. The patch is oriented so that the adhesive layer 124 faces in the direction toward the flange 140. Thus, it faces in the same direction as does the adhesive layer 118 of patch 106. The two patches are held in place on sleeve 112 by retaining ring 116 which has a sliding fit on the sleeve. Its dimensions are such that it will remain in contact with the tab unless forcibly pried away.

The outside diameter of the clamping sleeve 114 is slightly smaller than the inside diameter of the outer sleeve 112. However, assembly of the clamping sleeve into the outer is possible because the clamping sleeve is slotted over most of its length. It is provided with two slots along diametric lines. One of those slots is visible in FIG. 13 where it is numbered 156. The other slot is visible in FIG. 14 where it is numbered 158. Because of the provision of those slots, the clamping sleeve can be pressed to effectively smaller outer diameter so that it can be inserted into the end of sleeve 112. Handling of the clamping sleeve is facilitated by the provision of a flange 160 at one end.

The inner diameter of the clamping sleeve is greater than the outer diameter of tube 102 when the clamping sleeve is in the relaxed condition it is shown to occupy in FIG. 14. However, the slots 156 and 158 are sufficiently wide to permit insertion of the clamping sleeve into the outer sleeve 112 in a degree that reduces the effective inside diameter of the clamping sleeve to a dimension less than the outer diameter of the tube. Because of that, the sleeve 112, and the patches 106 and 108 can be fixed to the tube at any point along the length of the tube simply by positioning the outer tube 112 at the required point and then pushing the clamping sleeve 114 into the sleeve 112 until the tubing is held tight without reducing the diameter of the tubing 102.

The material from which the clamping ring 116 and the patch sheets 120 and 126 are formed has sufficient lubricity to permit the surfaces of tab 128 to slide over the adjacent surfaces of tab 106 and clamping ring 116. Because of that, the patch 108 can be rotated, relative to patch 106 and the fastening element, about the axis of tab opening 150 and the fastening element 110. Because of that feature, the patch 108 can be rotated relative to patch 106 so that the elongated portions extend substantially in parallel as they are shown to do in FIG. 10. On the other hand, patch 108 can be rotated completely through 360°. FIG. 17 illustrates one of the many positions that the patches can occupy relative to one another.

The patches are ordinarily made of a flexible material which can be bent out of the plane of their tabs either toward the end 104 of the tube, or away from it. Thus, it will be apparent that a very wide variety of physical arrangements is possible when the invention is applied to a subject.

The adhesive patches serve to fix the fastening element to the subject next to the body opening. The fastening element is made adjustable so the degree in which the tube end extends into the subject can be adjusted with ease. Ordinarily, the element by which the tubing is connected to the external apparatus is made so that it is easily attached to and removed from the tube. After the fastening member and adhesive patches are fixed in position around the tubing, the tube is cut to length and the attaching means by which the tube is connected to the external apparatus is reassembled on the tube. That was explained above in connection with FIG. 1.

That external apparatus may have a number of forms. In many cases, it will include an opening to which the intubation set is to be connected. That opening will have one of several standard sizes. The arrangement shown in FIG. 11 is typical. The transparent tubing 170 is part of the breathing port of a respiration control apparatus. It is Y-shaped, one branch transporting respiratory gas and the other conducting exhalation products away. The inner diameter is a standard dimension. In this embodiment, the connecting element 172 is a cup shaped structure which has a cup wall that may be inserted into the stem tube 170 with a sliding fit. The cup has cylindrical side walls 174 and it has a bottom wall 176. The outer diameter of the cup wall is reduced somewhat in the region of 178 next to the bottom wall to facilitate insertion into the tube 170. At its rim edge, the cup wall is provided with an outwardly extending flange 180 which is used as a finger hold to facilitate insertion into and removal from the tube 170.

The bottom wall 176 is formed with a central opening through which a sleeve 182 extends. The sleeve is bonded to the margins of the opening such as to form a seal completely around the sleeve 182. In this embodiment, the sleeve 182 and the cup are integrally formed of plastic.

The sleeve is longer than the cup is deep. Its outer end 184 lies outside of the cup wall 174 sufficiently far so that it can be readily seen and held whereby to facilitate insertion of the tube 102. Sleeve 182 extends from its end 184 through the cup and a short distance beyond the bottom wall 176 of the cup. The part that extends beyond the bottom wall is identified by the reference numeral 186. It serves in conjunction with the bottom wall 176 to form a trap against the entry into sleeve 182 and tube 102 of liquid that might condense on and run down the inner wall of tube 170. In applications where it is a liquid that is to be supplied to the subject, the trap extension 186 performs no function.

It is important for proper operation of the connecting element that the bottom wall 176 serve as a flexible diaphragm. It permits tilting of the sleeve 182 so that the sleeve axis is no longer coincident with, or parallel to, the axis of the cup wall. That tilting is permitted without any collapse of the sleeve 182. The purpose of the connector is to:

effect a connection between the tube 102 and the external apparatus to which the tube is to be connected;

to minimize changes in the degree of separation of the attaching member and the connecting member;

to permit angular or tilting movement of the tube 102 relative to the tube 170; and to minimize the volume of the flow path between the subject and the junction of the inhalation and exhalation flow paths whereby there is minimum dilution of the respiratory gas by exhalation products while permitting the inclusion of the water trap.

The combination of a cup construction with a central tube connected to the cup bottom provides a number of advantages in addition to flexibility. The cup wall being relatively long, provides a large sealing surface. The fact that the diaphragm, or bottom wall 176, is inserted up into the external tube 170 means that the tilt point is removed a maximum distance from the fastening element 110 for maximum flexibility; and, the fact that the cup wall may be placed adjacent the junction point in the Y-connector minimized the dead volume.

In the preferred embodiments, the connecting cup, the tube and the fastening element are all formed of resilient material to facilitate handling and set up, and to permit movement of the subject without adversely effecting the function of the set. Further, in the preferred embodiment, these elements are made transparent so that the assembly can be inspected readily for proper set up and operation.

The two embodiments shown in the drawings are employed in substantially the same fashion when they are to be used in conjunction with a respirator to conduct respiratory gas to, and to remove exhalation products from, a patient. The end of the gas flow tube should be placed at a point about two centimeters below the vocal chords in the patient's trachael tube. The distance from his lips to that point is estimated and the patches of the fastening element are moved along the tube to a point at the estimated distance from the end of the tube. The fastening element is then clamped to the tube with the patches located at that point. It may be desirable to trim the patch and cut it to shape in view of the contour of the patient's skin in the region at which it is to be attached. The flow tube is then inserted into the patient's trachea and the patch is attached to his lips or nose. The end of the endotracheal tube should be examined with a laryngoscope, or stethoscope or with X-ray apparatus to verify that its end is approximately two centimeters below the vocal chords. If readjustment is nessary, it is accomplished easily by withdrawing the clamping sleeve of the fastening element, moving the tube in appropriate degree relative to the outer tube and patch and then reinserting the inner clamp member so that the tube is again clamped relative to the fastening element. Finally, the outwardly extending part of the flow tube is cut to length and the end connector is assembled to it and to the respiratory apparatus.

The embodiment shown in FIGS. 18 through 22 is arranged so that the fastening means and the adhesive patch may be attached to the tube after the tube has been inserted into the subject's trachea. As in the case of the other embodiments, the adhesive patch is fixed to a fastening means such that the plane of the patch is perpendicular to the axis of the tube once the fastening means has been assembled on the tube. As in the other embodiments, the patch is fastened to the fastening means by a section that hinges and the hinge lies in the plane of the patch whereby the portion of the patch that bears the pressure sensitive adhesive may be bent upwardly or downwardly at an angle with that plane. As in the other embodiments, the fastening means in this embodiment is formed by two sleeves. The two sleeves are telescoped together and the inner diameter of the outer sleeve, or the first sleeve, is slightly smaller than the relaxed outer diameter of the inner sleeve. The walls of the inner, or second sleeve, are forced inwardly to clamp against the tube when the sleeves are telescoped together.

Referring to FIG. 18, the numeral 400 designates the tube. The tube shown is intended for insertion into subject's trachea. Its lower end 402 is cut off on the bias. The tube is made of a pliant elastomeric material. Its upper end is shown in section in FIG. 18 and it is shown to have a small spreader collar 404 inserted into the upper end of the tube so that its upper end is substantially even with the upper rim of the tube 400. The inside diameter of that spreader washer is substantially the same as the relaxed inside diameter of the tube 400. Its function is to stretch the upper end of the tubes to greater outside diameter so that it will be retained in the nipple 406 which is integrally formed with, and extends upwardly from, the bottom wall 408 of a cup-shaped connection element which corresponds generally to the connection element 172 shown in FIGS. 10, 11 and 12. The nipple 406 is formed with an outwardly protruding annular bulge into which the stretched end of the tube 400 and the expansion sleeve 404 are located. In FIG. 18, the connection element 408 has been moved downwardly away from the end of the tube so that it will be apparent that the nipple 406 is shaped with a bulge to receive the large end of the tube.

The nipple 406 extends so that its axis is coincident with the axis of the cup and it extends outside of the cup. As in the case of connection element 172, this connection element is assembled on the tube so that the tube extends through the cup-shaped portion of the connector. That is a feature of the invention, and its purpose is to provide a cup-shaped connector, or stopper, that will fit into the connector of a respiratory device, or other apparatus, while leaving no storage space, or dead space, within the connector. For example, if the connector 408 is moved upwardly relative to the tube so that the expanded end fits within the nipple 406 and the connector is then inserted into the mouth of a respiratory system Y-fitting, the fact that the connector is inserted into the fitting minimizes, or eliminates, any dead space in the fitting, whereby the upper end of the tube 400 is placed directly in the flowpath of fresh respiratory gas. The same construction, when so inserted into the outlet fitting of a respiratory system, has the nipple 406 arranged so that it projects above the flexible wall 408. Thus arranged, it cooperates with the fitting wall, or respiratory outlet, to form a liquid trap in the region below its upper rim.

The bottom wall 407 of the connector 408 is flexible whereby to permit angular movement of the tube relative to the outer wall of the cup 408 and the fitting in which it is inserted. The fact that the tube extends through the cup means that the distance from the point of connection with the connecting element to the point at which the fastening element is secured is increased. It is increased by an amount approximately equal to the depth of the cup. Since the tube is resilient, that increased length accounts for greater flexibility in the connection without having to increase the degree of flexibility in the tube itself by constructing it of a more flexible, and therefor more easily collapsible, material.

The fastening element is generally designated by the reference numeral 416. It is formed by a first sleeve, or an outer sleeve 418, and a second sleeve, or inner sleeve 420. The first sleeve is shown in top plan view in FIG. 21. It comprises a generally cylindrical sleeve 422 which has a flange 424 projecting outwardly from the cylinder at one end of the latter. The cylinder 422 is not complete. It is formed with a cutout, or slot, which extends longitudinally over the length of the sleeve. The side walls of the slot are designated by the reference numerals 426 and 428. The slot extends in the sleeve 422 and the flange 424 entirely through the wall of the cylinder and flange so that it opens to the central bore, or hole, through the sleeve. The wall of the bore is identified by the reference numeral 430. It has an inside diameter just slightly smaller than the relaxed outside diameter of the second, or inner, sleeve 420. That sleeve also is formed with a slot that extends longitudinally of the sleeve and opens to the central opening of the sleeve.

Returning to FIG. 21, a key, 432, is integrally formed with the first sleeve on the interior wall 430. In this embodiment, that key is located directly opposite the slot marked by walls 426 and 428. It extends over the entire length of the sleeve and its inner surface is arcuate so that it describes a segment of a circle whose diameter is approximately equal to the outside diameter of the tube 400. In this embodiment, the flange 424 is generally oblong in shape so that, rather than the usual circular flange appearance, this one looks like a pair of ears that extend is opposite directions from the end of the sleeve in the direction perpendicular to the key 32 and the slot.

The second, or inner, sleeve 420 is visible in FIGS. 18, 19 and 20. In includes a cylindrical sleeve portion 440 and a flange 442. The inner wall 444 has an inside diameter equal to or slightly greater than the tube 400. The flange 442 extends laterally from the sleeve 440 on a plane perpendicular to the axis of the bore through the sleeve. As in the case of the first sleeve, this second sleeve is slotted. Both the sleeve portion 444 and the flange 442 are slotted, and the slot extends entirely through the flange and through the wall. The walls of the sleeve that mark the edge of the slot are designated by the reference numerals 446 and 448. Those two walls are substantially parallel and they are separated a distance approximately equal to or slightly greater than the diameter of the tube 400. The member 418 may be moved laterally over the tube, or the tube 400 may be inserted into the slot of member 418, whereby the tube is lodged in the bore of the sleeve. That having been done, the first sleeve 418 may also be assembled on the tube 400 at a point on the tube at the side of the second sleeve unit 420 away from flange 442. The first sleeve 418 is then rotationally oriented so that its key 432 is aligned with the slot formed by walls 446 and 448 of the sleeve portion 440 of the second sleeve member 420. Thereupon, the first sleeve unit 418 is assembled on the second sleeve unit by presenting it down toward the second sleeve unit. The two sleeves telescope together. Wall 430 of the first sleeve fits over the outside wall of the sleeve portion 440 of the second sleeve unit, and being smaller diameter, pinches the sleeve 400 and forces it into clamping engagement with the tube 400. To facilitate that clamping action, the sleeve portion 440 is formed with a second slot 450. It extends through the wall of the sleeve 400 on the side opposite of the slot marked by walls 446 and 448. The slot 450 is much narrower than the opposite, tube entry slot. In the preferred embodiment, the slot 450 extends substantially the entire length of the sleeve 440 from its upper margin down to the vicinity of the flange 442.

The manner in which the first and second sleeve elements are oriented and assembled one with the other is illustrated both in FIGS. 18, 20 and 23. In FIGS. 20 and 23, the key 432 is shown to be in alignment with the slot of the second sleeve element. While it is visible in FIG. 19, the preferred embodiment includes a small handle by which the second sleeve unit can be grasped whereby the force used to assemble the two sleeves can be opposed by something other than by pressing against the subject. In this case, the handle has the shape of a paddle. It is located at one side of the flange 420 and extends in the plane of the central axis of the fastening element in the direction from the second sleeve unit toward the first sleeve unit. That handle is identified by the reference numeral 454. When sleeve 418 is pressed down over sleeve 420, the slot 450 is pinched closed. If excessive force is used, the tube 400 is not collapsed. Instead, the walls 426 and 428 of sleeve 418 separate.

In this embodiment, the patch is H-shaped. The fastening element is fixed to the cross bar of the H-shape and the slot formed by walls 446 and 448 extend parallel between the two arms 456 and 458 of the patch. The cross bar 460 is slotted and is formed with a central opening which is aligned with the slot and central opening of sleeve section 420. Referring to FIG. 18, the lower side of the two arms 456 and 458 are covered with a layer of pressure sensitive adhesive material 462 in the case of arm 456 and 464 in the case of arm 458. The undersurface of that adhesive is covered by a protective layer of plasticized material which protects the adhesive, but can be easily peeled away. The protective layer over adhesive layer 462 is designated by the reference numeral 470 and the protective layer associated with the other arm 458 is designated 472.

As best shown in FIG. 20, the flange 442 is formed in two pieces. The lower portion 476 in FIG. 18 (the portion at the right in FIG. 20) has a larger diameter than the upper portion, or the portion 478 at the right in FIG. 20. The central opening in the cross bar 460 of the patch has a diameter such that it fits over the flange section 478 and rests atop the flange section 476. The patch and the lower part of the flange having been assembled is shown in FIG. 20, the flange is completed by bonding a ring 480 against the shoulder formed by the stepped diameter of portions 476 and 478.

Unlike the embodiment described in FIGS. 10 through 17, the patch here is H-shaped, rather than being formed of two separate T-shape patches. In some instances, both of the arms 456 and 458 are useful, and the patch is used just as it is shown after the protective layers are peeled away from the adhesive side. However, for most applications, one of the two arms, or at least half of one of the arms, is unneeded or unwanted. In the preferred embodiment, the patch is made of a material that is easily cut with a nurse's scissors. The unwanted portion is simply cut away and discarded. The embodiment of FIGS. 18 through 20 is particularly useful in those instances where it is desired to remove the tube or to change the degree of insertion without removing the fastening means. Because the tube can be inserted in the fastening element by a lateral motion, it is unnecessary when inserting a tube, or changing the depth of insertion, to insert the tube by threading it through the fastening element. Instead, it can be inserted without regard to the fastening element, and when at proper depth, simply moves laterally into the slot. The fastening element is then clamped by telescoping the two sleeve units together and the job is done.

Although I have shown and described certain specific embodiments of my invention, I am fully aware that many modifications thereof are possible. My invention, therefore, is not to be restricted except insofar as is necessitated by the prior art.

I claim:

1. For use in holding an apparatus in position in front of a subject's body opening:
    fastening means in the form of a fastening element for holding said apparatus;
    adhesive means in the form of a patch of flexible sheet material attached at one of its edges to said fastening means and being capable of adhering to an area of the subject's skin around that opening; and
    a tube carried by said fastening means and having internal resilience biasing the tube toward arcuate shape along its length;
    said fastening means being effective to hold said tube such that it extends through the plane of said patch;
    said fastening means comprising a sleeve formed with a bore through which said tube extends, and in which said patch extends sidewardly from one end of said sleeve and has a flexible connection to said sleeve whereby the patch can bend from a position in the plane perpendicular to the axis of said bore to tilted positions above and below said plane.

2. The invention defined in claim 1 which further comprises a connecting means for connection to one end of said tube, at the side of said sleeve opposite the patch, said connecting means comprising a flexible conduit, a connector fitting fixed to one end of the flexible conduit, and a coupling at the other end of said conduit, said coupling having outer diameter larger than said bore of the sleeve, and into which said one end of said tubing is insertable.

3. The invention defined in claim 1 in which said patch has the form of a strip of flexible material having flexible connection to said sleeve at the mid-region of one edge of the strip.

4. For use in holding an apparatus in position in front of a subject's body opening:
    fastening means in the form of a fastening element for holding said apparatus;
    adhesive means in the form of a patch of flexible sheet material attached at one of its edges to said fastening means and being capable of adhering to an area of the subject's skin around that opening;
    said adhesive means comprising two patches of material each attached at one of its edges to said fastening means and extending from said fastening means substantially in the same plane, a first one of said patches being rotatable in said plane about said fastening means relative to the other of said patches; and
    said fastening means comprising a sleeve formed with an annular shoulder at a point along its length;
    a second one of said patches comprising a tab extending from one of its edges, said tab being formed with an opening to receive said sleeve and having a layer of adhesive on an area of said tab adjacent to said opening, said layer of adhesive having bonding contact with said shoulder whereby said second patch is held against rotation relative to said sleeve.

5. The invention defined in claim 4 in which said sleeve is formed with a flange at one end of said sleeve and said shoulder is formed by a surface of said flange, said layer of adhesive on the tab adjacent to said opening being in contact with said flange;

both of said patches having surface areas facing said flange covered with a layer of adhesive material.

6. In an intubation set:

fastening means in the form of a fastening element having a bore through which a tube can extend;

adhesive means in the form of a patch of flexible sheet material attached at one of its edges to said fastening means and being capable of adhering to an area of the subject's skin around a body opening;

said patch extending sidewardly from said fastening element in a plane perpendicular to the axis of said bore and having a flexible connection to said fastening means such that the patch can be bent at said connection from a position in the plane perpendicular to the axis of said bore to tilted positions above and below that plane;

said fastening means comprising at least two pieces engageable with one another and said adhesive means.

7. In an intubation set:

fastening means in the form of a fastening element having a bore through which a tube can extend;

adhesive means in the form of a patch of flexible sheet material attached at one of its edges to said fastening means and being capable of adhering to an area of the subject's skin around a body opening;

said patch extending sidewardly from said fastening element in a plane perpendicular to the axis of said bore and having a flexible connection to said fastening means such that the patch can be bent at said connection from a position in the plane perpendicular to the axis of said bore to tilted positions above and below that plane;

said fastening means comprising first and second sleeves through which a tube may extend, said first sleeve of which fits over the second and has an inside diameter exceeding the outside diameter of said second sleeve;

said second sleeve being formed with an opening along one side extending in the direction of its axis whereby the inside diameter of said second sleeve is reduced upon being assembled with said first sleeve;

said second sleeve and said flange being formed with a longitudinal slot extending parallel to the axis of said sleeve and extending to the opening therethrough whereby said second sleeve may be assembled with a tube such that the axis of the tube is substantially coincident with the opening through said second sleeve by movement of the tube through said slot into said opening;

said first sleeve being formed with a longitudinal slot extending in the direction of the axis of the opening through said sleeve, said slot extending entirely through the wall of said first sleeve and having a size to accommodate a tube of size to fit within said opening through said second sleeve;

a tube disposed in the opening of said first and second sleeves of said fastening means; and connecting means connected to one end of said tube, said connecting means comprising a cup having a flexible bottom wall, a nipple fixed to the bottom wall of said cup and extending axially therefrom outside of the cup, said tube having its end in communication with said nipple and extending through said cup.

8. The invention defined in claim 7 in which the nipple of said connecting means is formed of an elastomeric material;

said invention further comprising means for expanding the outer dimension of said tube in the region thereof that is disposed within said nipple.

9. An intubation set comprising:

a tube;

fastening means for holding the tube such that a point along its length may be disposed adjacent the body opening of a subject;

means in the form of a patch of flexible sheet material, said patch being attached at one of its edges to said fastening means and being capable of adhering to an area of the subject's skin around said body opening;

connection means for connecting an end of said tube in an opening larger than the outer diameter of the tube;

said connection means comprising a cup having generally cylindrical side walls, a bottom wall formed with a central opening, and a sleeve forming an end portion of said tube, said sleeve being fastened to said bottom wall of the margins of its central opening, the sleeve extending entirely through the cup and the cup opening in the direction of said fastening means whereby the cup serves to reduce the ullage volume within a container with which it is associated.

10. An intubation set comprising:

a tube;

fastening means for holding the tube such that a point along its length may be disposed adjacent the body opening of a subject;

connection means for connecting an end of said tube in an opening larger than the outer diameter of said tube;

said connection means comprising a cup having generally cylindrical side walls, a flexible bottom wall formed with a central opening, and a sleeve forming an end portion of said tube, said sleeve being fastened to said bottom wall at the margins of its central opening whereby said bottom wall serves as a flexible diaphragm permitting tilting of said sleeve such that the axis of the sleeve is tilted relative to the central axis of said cup, the tube extending entirely through the cup;

said sleeve extending through the bottom wall of said cup whereby one end thereof serves as a liquid trap in conjunction with said bottom wall when the cup is inserted in the mouth of a container; and said fastening means further comprising adhesive means in the form of two patches of material each attached at one of its edges to said fastening means and extending therefrom substantially in the same plane, at least one of said patches being rotatable in said plane about said fastening means relative to the other of said patches.

11. The invention defined in claim 10 in which said tube, said connection means and said fastening means are formed of transparent, resilient material.

12. An intubation set comprising:

a tube;

fastening means for holding the tube such that a point along its length may be disposed adjacent the body opening of a subject;

connection means for connecting an end of said tube in an opening larger than the outer diameter of the tube;

said connection means comprising a cup having generally cylindrical side walls, a bottom wall formed with a central opening, and a sleeve forming an end portion of said tube, said sleeve being fastened to said bottom wall at the margins of its central opening, the sleeve extending entirely through the cup and the cup opening in the direction of said fastening means whereby the cup serves to reduce the ullage volume within a container with which it is associated; and a respiratory apparatus having an opening from which respiratory gas may be drawn and to which respiratory gas may be returned;

said cup being disposed in said opening with the inside of the cup opening toward the direction away from the interior of said respiratory apparatus and toward said fastening element.

* * * * *